(12) United States Patent
Zhang et al.

(10) Patent No.: US 9,012,477 B2
(45) Date of Patent: Apr. 21, 2015

(54) METHOD OF TREATING NEUROPATHIC PAIN

(75) Inventors: Jie Zhang, Salt Lake City, UT (US); Robert Lippert, Park City, UT (US)

(73) Assignee: Nuvo Research Inc., Mississauga, Ontario (CA)

(*) Notice: Subject to any disclaimer, the term of this patent is extended or adjusted under 35 U.S.C. 154(b) by 71 days.

(21) Appl. No.: 12/652,502

(22) Filed: Jan. 5, 2010

(65) Prior Publication Data

US 2011/0015229 A1    Jan. 20, 2011

Related U.S. Application Data

(60) Provisional application No. 61/142,662, filed on Jan. 6, 2009.

(51) Int. Cl.
| | | |
|---|---|---|
| A61K 31/445 | (2006.01) | |
| A61K 31/245 | (2006.01) | |
| A61P 23/02 | (2006.01) | |
| A61K 31/24 | (2006.01) | |
| A61K 9/70 | (2006.01) | |
| A61K 31/167 | (2006.01) | |
| A61K 47/32 | (2006.01) | |

(52) U.S. Cl.
CPC .............. *A61K 31/24* (2013.01); *A61K 9/7015* (2013.01); *A61K 31/167* (2013.01); *A61K 47/32* (2013.01)

(58) Field of Classification Search
CPC ..... A61K 31/167; A61K 31/24; A61K 47/32; A61K 9/7015; A61K 9/0034; A61K 2300/00
USPC .......................................... 514/330, 535, 636
See application file for complete search history.

(56) References Cited

U.S. PATENT DOCUMENTS

| | | | |
|---|---|---|---|
| 3,929,131 A | 12/1975 | Hardwick | |
| 4,230,105 A | 10/1980 | Harwood | |
| 4,286,592 A | 9/1981 | Chandrasekaran | |
| 4,529,601 A | 7/1985 | Broberg et al. | |
| 4,685,911 A | 8/1987 | Konno et al. | |
| 4,693,706 A | 9/1987 | Ennis, III | |
| 4,695,465 A | 9/1987 | Kigasawa et al. | |
| 4,747,841 A | 5/1988 | Kuratomi et al. | |
| 4,780,320 A | 10/1988 | Baker | |

(Continued)

FOREIGN PATENT DOCUMENTS

| | | |
|---|---|---|
| CA | 2228137 | 2/1997 |
| CA | 2408585 | 2/1997 |

(Continued)

OTHER PUBLICATIONS

Polymer article, downloaded from the internet on Aug. 11, 2014, http: https://web.archive.org/web/20070712124323/http://chemed.chem.purdue.edu/genchem/topicreview/bp/1polymer/types.html.*

(Continued)

*Primary Examiner* — Savitha Rao (57) ABSTRACT

A method for treating subjects experiencing neuropathic pain is provided. The method involves the application of a solid-forming local anesthetic formulation to a skin surface of the subject experiencing the neuropathic pain and then maintaining the formulation on the skin surface for a period of time sufficient to allow itself to transdermally deliver the local anesthetic to the subject thereby providing relief from the neuropathic pain within about 45 minutes.

19 Claims, 2 Drawing Sheets

(56) References Cited

U.S. PATENT DOCUMENTS

| | | | |
|---|---|---|---|
| 4,830,855 A | 5/1989 | Stewart | |
| 4,879,119 A | 11/1989 | Konno et al. | |
| 4,898,592 A | 2/1990 | Latzke et al. | |
| 4,911,707 A | 3/1990 | Heiber et al. | |
| 4,913,957 A | 4/1990 | Strack et al. | |
| 4,963,360 A | 10/1990 | Argaud | |
| 4,994,049 A | 2/1991 | Latzke et al. | |
| 5,108,710 A | 4/1992 | Little et al. | |
| 5,114,411 A | 5/1992 | Haber et al. | |
| 5,128,137 A | 7/1992 | Muller et al. | |
| 5,147,339 A | 9/1992 | Sundstrom | |
| 5,213,129 A | 5/1993 | Someah et al. | |
| 5,217,718 A | 6/1993 | Colley et al. | |
| 5,229,133 A | 7/1993 | Wright et al. | |
| 5,276,032 A | 1/1994 | King et al. | |
| 5,279,594 A | 1/1994 | Jackson | |
| 5,329,976 A | 7/1994 | Haber et al. | |
| 5,330,452 A | 7/1994 | Zook | |
| 5,364,350 A | 11/1994 | Dittmann | |
| 5,370,879 A | 12/1994 | Masterson et al. | |
| 5,378,730 A | 1/1995 | Lee et al. | |
| 5,658,583 A | 8/1997 | Zhang et al. | |
| 5,733,572 A | 3/1998 | Unger et al. | |
| 5,776,952 A | 7/1998 | Liedtke | |
| 5,840,755 A | 11/1998 | Liedtke | |
| 5,885,597 A | 3/1999 | Botknecht et al. | |
| 5,906,814 A | 5/1999 | Epstein | |
| 5,919,479 A | 7/1999 | Zhang et al. | |
| 5,993,836 A | 11/1999 | Castillo | |
| 6,036,966 A | 3/2000 | Youssefyeh | |
| 6,211,250 B1 | 4/2001 | Tomlinson et al. | |
| 6,245,347 B1 | 6/2001 | Zhang et al. | |
| 6,261,595 B1 | 7/2001 | Stanley et al. | |
| 6,303,142 B1 | 10/2001 | Zhang et al. | |
| 6,306,431 B1 | 10/2001 | Zhang et al. | |
| 6,324,424 B1 | 11/2001 | Ledger et al. | |
| 6,340,472 B1 | 1/2002 | Zhang et al. | |
| 6,453,648 B1 | 9/2002 | Zhang | |
| 6,465,006 B1 | 10/2002 | Zhang et al. | |
| 6,465,709 B1 | 10/2002 | Sun et al. | |
| 6,488,959 B2 | 12/2002 | Stanley et al. | |
| 6,528,086 B2 | 3/2003 | Zhang | |
| 6,546,281 B1 | 4/2003 | Zhang et al. | |
| 6,613,350 B1 | 9/2003 | Zhang et al. | |
| 6,756,053 B2 | 6/2004 | Zhang et al. | |
| 6,756,426 B2 | 6/2004 | Brother et al. | |
| 6,780,426 B2 | 8/2004 | Zhang et al. | |
| 6,955,819 B2 | 10/2005 | Zhang et al. | |
| 7,063,859 B1 | 6/2006 | Kanios et al. | |
| 2002/0004063 A1 | 1/2002 | Zhang | |
| 2005/0075407 A1 | 4/2005 | Tamarkin et al. | |
| 2005/0209319 A1 | 9/2005 | Cundy | |
| 2005/0239868 A1 | 10/2005 | Shirai et al. | |
| 2006/0147510 A1 | 7/2006 | Galer | |
| 2007/0059351 A1 | 3/2007 | Murrell et al. | |
| 2007/0068508 A1 | 3/2007 | York-Leung Wong | |
| 2007/0189978 A1 | 8/2007 | Zhang et al. | |
| 2007/0196323 A1 | 8/2007 | Zhang et al. | |
| 2007/0196458 A1 | 8/2007 | Zhang et al. | |
| 2007/0299540 A1 | 12/2007 | Ku | |
| 2008/0021051 A1 | 1/2008 | Wilson | |
| 2008/0260655 A1 | 10/2008 | Tamarkin et al. | |
| 2011/0015229 A1 | 1/2011 | Zhang et al. | |

FOREIGN PATENT DOCUMENTS

| | | |
|---|---|---|
| DE | 2851369 | 6/1979 |
| EP | 0386960 | 9/1990 |
| EP | 0455396 | 11/1991 |
| EP | 0770387 | 10/1995 |
| EP | 2205496 | 4/2009 |
| EP | 2163956 | 3/2010 |
| GB | 2163959 | 3/1986 |
| JP | 62051617 | 3/1987 |
| JP | 52-79018 | 10/1993 |
| JP | 3547453 | 7/2004 |
| WO | WO88/09169 | 12/1988 |
| WO | WO 88/09169 | 12/1988 |
| WO | WO92/13529 | 8/1992 |
| WO | WO96/19453 | 6/1996 |
| WO | WO 97/04728 | 2/1997 |
| WO | WO97/15548 | 5/1997 |
| WO | WO97/38675 | 10/1997 |
| WO | WO99/22717 | 5/1999 |
| WO | WO 00/18339 | 4/2000 |
| WO | WO 01/22907 | 4/2001 |
| WO | WO 04/000358 A1 | 12/2003 |
| WO | WO 2005/120473 A2 | 12/2005 |
| WO | WO2007/070679 | 6/2007 |
| WO | WO 2007/070679 | 6/2007 |
| WO | WO 2008/150995 | 12/2008 |
| WO | WO2008/150995 | 12/2008 |
| WO | WO 2009/053572 | 4/2009 |
| WO | WO 2010/080831 | 7/2010 |
| WO | WO 2010/114973 | 10/2010 |
| WO | WO 2010/129542 | 11/2010 |
| WO | WO 2011/088333 A2 | 7/2011 |

OTHER PUBLICATIONS

Biological polymers, downloaded from the internet on Aug. 11, 2014, http: http://www.employees.csbsju.edu/ssaupe/biol121/chem_biol.htm.*

Local anesthetics (downloaded from the internet on Aug. 11, 2014, http: https://web.archive.org/web/20120906202800/http://www.ifna-int.org/ifna/e107_files/downloads/lectures/H1LocalAne.pdf.*

Hoshino et al.; Preparation of a Local Anesthetic Ointment Containing the Eutectic Mixture of Lidocaine and Tetracaine; 1991; vol. 51, No. 3 p. 158-165 (abstract only).

Kawano et al.; Comparison of Analgesic Effect of Lidocaine Tape Versus Eutectic Mixture of Lidocaine and Tetracaine During Infiltration of Local Anesthetics before Epidural Block; Sep. 1996; vol. 45 No. 9; pp. 1074-1077 (abstract only).

Astra USA, Inc., "Elma Cream (lidocaine 2.5% and prilocaine 2.5%)", Product Information Form for American Hospital Formulary Service, 1993, p. 1-28.

Knutson et al., "Solvent-Mediated Alterations of the Stratum Corneum", Journal of Controlled Release vol. 11, 1990, p. 93-103.

Lycka, "EMLA, a New and Effective Topical Anesthetic", J. Dermotol. Surg. Oncol., vol. 18,1992, p. 859-862.

Mack Publishing Company, "Stability of Pharmaceutical Products", Pharmaceutical Sciences, p. 1481-2,1985.

McCafferty et al., Comparative In Vivo and In Vitro Assessment of the Percutaneous Absorption of Local Anaesthetics:, Br. J. Anasth., vol. 60, 1988, p. 64-69.

McCafferty et al., "In Vivo Assessment of Percutaneous Local Anesthetic Preparations", Br. J. Anaesth., vol. 62, 1989, p. 18-21.

McCafferty et al., "New Patch Delivery System for Percutaneous Local Anesthesia", Br. J. Anaesth., vol. 71, 1993, p. 370-374.

Sakamoto et al., "Dermal Patch Anesthesia: Comparison of 10% Lignocaine Gel with Absorption Promoter and EMLA Cream", Anesthesia, vol. 48, 1993, p. 390-392.

Woolfson et al., "Concentration Response Analysis of Percutaneous Local Anesthetic Formulations", BR. J. Anaesth., vol. 61, 1988, p. 590-592.

Woolfson, "Percutaneous Local Anesthesia", Formulation of Local Anesthsia for Percutaneous Delivery (Ch. 5), E. Horwood, NY, 1993 p. 166-170.

(56) References Cited

OTHER PUBLICATIONS

U.S. Appl. No. 12/752,384, filed Apr. 1, 2010; Jie Zhang.

U.S. Appl. No. 12/773,239, filed May 4, 2010; Jie Zhang.

Young et al; What's New in Topical Anesthesia; Clinical Pediatric Emergency Medicine; Dec. 3, 2007; pp. 232-239; vol. 8, No. 4.

Cada et al.; Lidocaine/Tetracaine Patch; Hospital Pharmacy; 2006; pp. 265-273; vol. 41 No. 3.

Argoff; A Review of the Use of Topical Analgesics for Myofascial Pain; a Review of the Use of Topical Analgesics for Myofascial Pain; 2002; pp. 375-378; vol. 6.

Ohzeki et al; Local Anethetic Cream Prepared from Lidocain-Tetracaine Eulecetic Mixture; Yakugaku Zasshi; 2008; pp. 611-616; vol. 128.

Yap, "Myofascial Pain—An Overview"; Ann Acad. Med. Singapore vol. 36, pp. 43-48, 2007.

Risovic, et al.; "Formulacija I Ispitivanje Rubeefacijentnog Dejstva Preparata Sa Kapsaicinom"; Lek Sirov. vol. XX (No. 21): 157-161, 2001.

\* cited by examiner

METHOD OF TREATING NEUROPATHIC PAIN

This application claims the benefit of U.S. Provisional Patent Application No. 61/142,662, filed Jan. 6, 2009.

BACKGROUND

Neuropathic pain can be caused by various diseases, such as viral infections and diabetes. For example, post herpetic neuralgia is caused by herpes viral infection and cause moderate to severe pain in the infected skin area to the subject. Various drugs and formulations have been used to treat neuropathic pain with varying degrees of success. There is an ongoing need to treat this type of pain, accordingly, research continues into methods of treating neuropathic pain in a manner that is rapid-acting and long lasting.

DETAILED DESCRIPTION

Before particular embodiments of the present invention are disclosed and described, it is to be understood that this invention is not limited to the particular process and materials disclosed herein as such may vary to some degree. It is also to be understood that the terminology used herein is used for the purpose of describing particular embodiments only and is not intended to be limiting, as the scope of the present invention will be defined only by the appended claims and equivalents thereof.

In describing and claiming the present invention, the following terminology will be used.

The singular forms "a," "an," and "the" include plural referents unless the context clearly dictates otherwise. Thus, for example, reference to "a drug" includes reference to one or more of such compositions.

"Skin" is defined to include human skin (intact, diseased, ulcerous, or broken), and mucosal surfaces that are usually at least partially exposed to air such as lips, genital and anal mucosa, and nasal and oral mucosa.

The term "substantially" as used herein is intended to describe quantities or other measures as a degree of completeness. For example, when referring to the evaporation of the water, "substantially" means a range from a majority of the water to all of the water which was included in the initial formulation has evaporated. "Substantially" as it relates to an entire duration refers to a period of time ranging from the nearly the entire duration to the entire duration (or even longer). The term "substantially" as it relates to a composition being free of solvents less volatile than water indicates that virtually no amount of these types of solvents are present, e.g., solvent content of this type ranges from only trace amounts to complete absence of non-volatile solvents.

The term "solid-forming local anesthetic formulation" or "solid-forming formulation" refers to a formulation that is in the state of a semisolid and comprises a local anesthetic, water, and a polymer before being applied onto a skin surface. After being applied to a skin surface as a thin layer (e.g., 1 mm thick), the solid-forming local anesthetic formulation forms a layer of a coherent solid after sufficient concentration of water is evaporated from the formulation layer. Examples of semi-solid forms include creams, ointments, pastes, viscous lotions, gels, and the like. It is notable that the solid-forming formulations of the present invention are free of backing layers and backing films and are formulated to be applied directly to a skin surface as a semi-solid state without the need of a separate support substrate (e.g. backing layer or backing firm) both before application and after being applied. The ability of the formulation to be applied directly to the skin without a backing layer, backing film, or other support substrate enhances the ability of the formulation to better adhere to regions of a subjects skin that do not readily lend themselves to traditional transdermal patches (i.e. those that include backing layers or backing films). By enhancing adherence to such surfaces, the solid-forming formulations are more effective in delivering therapeutically effective amounts of the local anesthetics, thereby providing enhanced relief of the neuropathic pain.

The phrases "sufficient amount of water" or "sufficient concentration of water" refers to an amount or a concentration of water evaporated from an applied layer of the formulation such formulation transitions from a semi-solid to a coherent solid.

"Coherent solid" or more specifically, a "coherent soft solid" describes the solidified layer of the solid-forming local anesthetic formulation after a sufficient concentration of water has evaporated (sufficient to cause the solidification). The coherent soft solid remains adhered to the skin, and is capable of maintaining good contact with the subject's skin for substantially the entire duration of desired application. Additionally, a "coherent solid," can have cohesive strength sufficient such that the solid remains intact when peeled from the skin. In other words, cohesive soft solids do not include lotions and other liquids that remain cohesive as liquids, but rather, includes compositions that remain at least partially cohesive in the solid state. In one embodiment, the coherent solid can be peelable from the skin.

The term "initial state" when used to describe a solid-forming local anesthetic formulation refers to the state of the formulation before being applied to a skin surface.

The term "neuropathic pain" refers to any and all types of neuropathic pain regardless of the cause. Examples of specific sources of neuropathic pain for which the methods of the present invention can be used include diabetic neuropathies and virus-caused neuropathies. The treatment of neuropathic pain as described herein refers to the alleviation or elimination of the neuropathic pain associated with a neuropathy.

The term "proximate" when referring to a location on a skin surface, particularly as it relates to the location of neuropathic pain, means an area of skin directly over (in part or fully covering) or immediately adjacent to tissue from which the neuropathic pain is present.

As used herein, a plurality of drugs, compounds, and/or solvents may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 0.01 to 2.0 mm" should be interpreted to include not only the explicitly recited values of about 0.01 mm to about 2.0 mm, but also include individual values and sub-ranges within the indicated range. Thus, included in this numerical range are individual values such as 0.5, 0.7, and 1.5, and sub-ranges such as from 0.5 to 1.7, 0.7 to 1.5, and from 1.0 to 1.5, etc. Furthermore, such an interpretation should apply regardless of the breadth of the range or the characteristics being described. Additionally, it is noted that all percentages are in weight, unless specified otherwise.

When referring to achieving an effect, the phrases such as "in most human subjects", "in human subject", "in most patients", and "in most human patients" mean achieving clinically meaningful levels of that effect in at least 70% of a group of at least 12 human subjects or patients when tested at room temperature.

It is also noted that "local anesthetics" in appropriate formulations can be used to provide skin "anesthesia," which by medical definition means preventing a pain before it happens, such as preventing a pain caused by needle stick. The present disclosure, however, is related to methods of using a local anesthetic formulation to provide "analgesia," which by medical definition means to reduce or eliminate an existing pain, such as neuropathic pain.

With this background in mind, a method of treating neuropathic pain in a subject is provided. The method includes applying a layer of a solid-forming local anesthetic formulation to a skin surface of a human experiencing neuropathic pain, and maintaining said formulation on said skin surface for a period of time sufficient to allow the formulation to transdermally deliver the local anesthetic to the subject and to transition from its initial state of semi-solid to a coherent soft solid after the evaporation of sufficient amount of water from the formulation. The solid-forming local anesthetic formulation in its initial state before being applied on the skin surface can include a local anesthetic agent, water, and a polymer, and can further be substantially devoid of any solvent more volatile than water. The solid-forming local anesthetic formulation can provide relief from said neuropathic pain within about 45 minutes after application to the skin surface.

The source or cause of the neuropathic pain treated by the methods of the present invention can vary. One example of neuropathic pain is pain associated with herpes or shingles, which can be treated in accordance with embodiments of the present disclosure. Other examples of sources of neuropathic pain include pain associated with diabetes, pain associated with postherpetic neuralgia, and pain associated with post-surgical/post-traumatic conditions.

The solid-forming local anesthetic formulations used in the methods of the present disclosure are in an initial semi-solid state before being applied to the skin surface. Non-limiting examples of semi-solid formulation states include creams, ointments, pastes, lotions, and the like. After application, the solid-forming local anesthetic formulation of the present disclosure forms a soft coherent solid layer after the evaporation of sufficient amount of water. Thus, the formulation starts as a semi-solid and forms a coherent soft solid over a relatively short period of time (typically 10-30 minutes). The solid-forming local anesthetic formulation can deliver the local anesthetic to the skin beginning with application to the skin surface and continuing until substantially all the water is evaporated from the formulation. Therefore, the delivery of the local anesthetic agent continues after the formation transforms into a layer of soft solid, because typically there is still significant amounts of water in the formulation layer when the formulation solidifies. After evaporation of substantially all the water, delivery of the local anesthetic often stops or slows significantly so as to have no therapeutic effect. As such, in one embodiment of the present disclosure, the solid-forming local anesthetic formulation can include at least about 15 wt % water. In another embodiment, the solid-forming local anesthetic formulation can include at least about 22 wt % water. In yet a further embodiment, the solid-forming local anesthetic formulation can include at least about 50 wt % water.

The evaporation rate of the water from the formulation can vary depending on the environment as well as the thickness of the layer of the solid-forming local anesthetic formulation applied to the skin. In one embodiment, the solid-forming local anesthetic formulation can form a soft coherent solid layer within about 15 minutes when it is applied with a thickness of about 0.5 mm. If the thickness of the applied formulation is too thick, the formulation may take longer to solidify, thereby causing some inconvenience to the user. If the thickness of the applied solid-forming local anesthetic formulation is too thin, the formulation may not provide the desired analgesic effect because the water in the formulation may evaporate too quickly. Accordingly, in one embodiment of the present invention, the solid-forming local anesthetic formulation can be applied as a layer with a thickness of from 0.1 to 3.0 millimeters. In another embodiment, the solid-forming local anesthetic formulation can be applied as a layer with a thickness of from 0.2 to 2.0 millimeters. In yet another embodiment, the solid-forming local anesthetic formulation can be applied as a layer with a thickness of from 0.3 mm to 1.5 mm.

Once applied, the solid-forming local anesthetic formulations of the present disclosure can be left on the skin surface, either as the semi-solid or as the soft coherent solid, for varying periods of time. In order for the solid-forming local anesthetic formulation to provide measurable relief of the pain, it is generally desirable that the formulation remain on the skin surface of the subject for a period of at least about 20 minutes, preferably for a period of at least about 60 minutes. In one embodiment, the solid-forming local anesthetic formulation is formulated to provide relief or elimination of neuropathic pain within about 45 minutes after application to the skin surface. Phases "relief of neuropathic pain", 'relief of pain", 'clinically relevant neuropathic pain reduction" are used interchangeably and are defined as an average reduction of 3 points or more from the baseline on an 11-point numeric pain rating scale compared with placebo when tested using at least 12 subjects Generally, the formulations used in the methods of the present invention are formulated to be maintained on the skin surface of the subject for a period of time of from about 45 minutes to about 2 hours. In some embodiments, the formulation may be left on the skin for periods extending beyond two hours. In one embodiment, the solid-forming local anesthetic formulation can be left on the skin for a period of from about 20 minutes to about 120 minutes, after which the formulation can be removed by washing, but typically by peeling the coherent soft solid from the skin. The duration of analgesic effect is dependent in part on the duration of time that the formulation is left on the skin. In one embodiment, the solid-forming local anesthetic formulation can be formulated to provide pain relief for at least 6 hours after an application time of at least 45 minutes.

The solid-forming local anesthetic formulations used in the methods of the present disclosure can include a variety of local anesthetics known in the art. Non-limiting examples of local anesthetics include tetracaine, lidocaine, prilocaine, ropivacaine, bupivacaine, and mixtures thereof. In one embodiment, the total local anesthetic concentration can be from about 4 wt % to about 15 wt % of the formulation. In one specific embodiment, the solid-forming local anesthetic formulation includes tetracaine in amounts from about 4 wt % to about 10 wt %, or in on embodiment, from about 6 wt % to about 8 wt % of the formulation. In another embodiment, the solid-forming local anesthetic formulation can include lidocaine in amounts from about 4 wt % to about 10 wt %, or in one embodiment, from about 6 wt % to about 8 wt % of the local anesthetic formulation. In a further embodiment, the local anesthetic agent in the solid-forming local anesthetic formulation can be a eutectic mixture of multiple base form local anesthetics, e.g., lidocaine and tetracaine.(each from about 4 wt % to 10 wt %, or from about 6 w % to about 8 wt %). It is noted that all concentrations of local anesthetics referenced in the current disclosure are weight concentrations before the formulation is applied on a skin surface. After the formulation is applied on a skin surface as a thin layer, water starts to evaporate and the concentration of the local anesthetic starts to increase. It is further noted that any single local anesthetic can be used, or any combination of local anesthetics can be used, provided the local anesthetic(s) promotes analgesia with respect to existing neuropathic pain. It is also noted that these local anesthetics can be present, and are often more effective, in their base form.

Polymers that can be used in the solid-forming local anesthetic formulations of the present disclosure include, but are not limited to polyvinyl alcohol, polyvinyl pyrrolidone, ethyl cellulose, mixtures thereof, and the like. The polymer or mixture of polymers assist in promoting the formation of the coherent soft solid upon evaporation of the water and/or other solvents that may be present in the formulation. Typical polymer concentrations in the solid-forming local anesthetic formulations of the current invention range from about 10 wt % to about 40 wt %. In one embodiment the polymer concentration can be from about 12 wt % to about 30 wt %.

EXAMPLES

The following examples illustrate the embodiments of the invention that are presently best known. However, it is to be understood that the following are only exemplary or illustrative of the application of the principles of the present invention. Numerous modifications and alternative compositions, methods, and systems may be devised by those skilled in the art without departing from the spirit and scope of the present invention. The appended claims are intended to cover such modifications and arrangements. Thus, while the present invention has been described above with particularity, the following examples provide further detail in connection with what are presently deemed to be the most practical and preferred embodiments of the invention.

Example 1

Solid-Forming Local Anesthetic Formulation

A solid-forming local anesthetic formulation according to one embodiment of the current invention was prepared according to the compositional formulation of Table 1:

TABLE 1

| Component | Weight Percentage (% w/w) |
|---|---|
| Lidocaine, USP (base) | 7 |
| Tetracaine, USP (base) | 7 |
| Dibasic Calcium Phosphate, Anhydrous, USP | 36 |
| Polyvinyl Alcohol, USP (Molecular Weight 31,000-50,000) | 12 |
| White Petrolatum, USP | 10 |
| Sorbitan Monopalmitate, NF (Span ® 40) | 2 |
| Methylparaben, NF | 0.05 |
| Propylparaben, NF | 0.01 |
| Purified Water, USP | Balance |

The formulation forms a coherent soft solid after application.

Example 2

Solid-Forming Local Anesthetic Formulation

Another solid-forming local anesthetic formulation according to one embodiment of the current invention was prepared according to the compositional formulation of Table 2:

TABLE 2

| Component | Weight Percentage (% w/w) |
|---|---|
| Lidocaine, USP (base) | 7 |
| Tetracaine, USP (base) | 7 |
| Corn starch | 20 |
| Polyvinyl Alcohol, USP (Molecular Weight 31,000-50,000) | 19.77 |
| Sorbitan Monopalmitate, NF (Span ® 40) | 3.3 |
| Methylparaben, NF | 0.08 |
| Propylparaben, NF | 0.02 |
| Purified Water, USP | Balance |

Example 3

Treatment of Neuropathic Pain Caused by Post Herpetic Neuropathy

Figure 1:
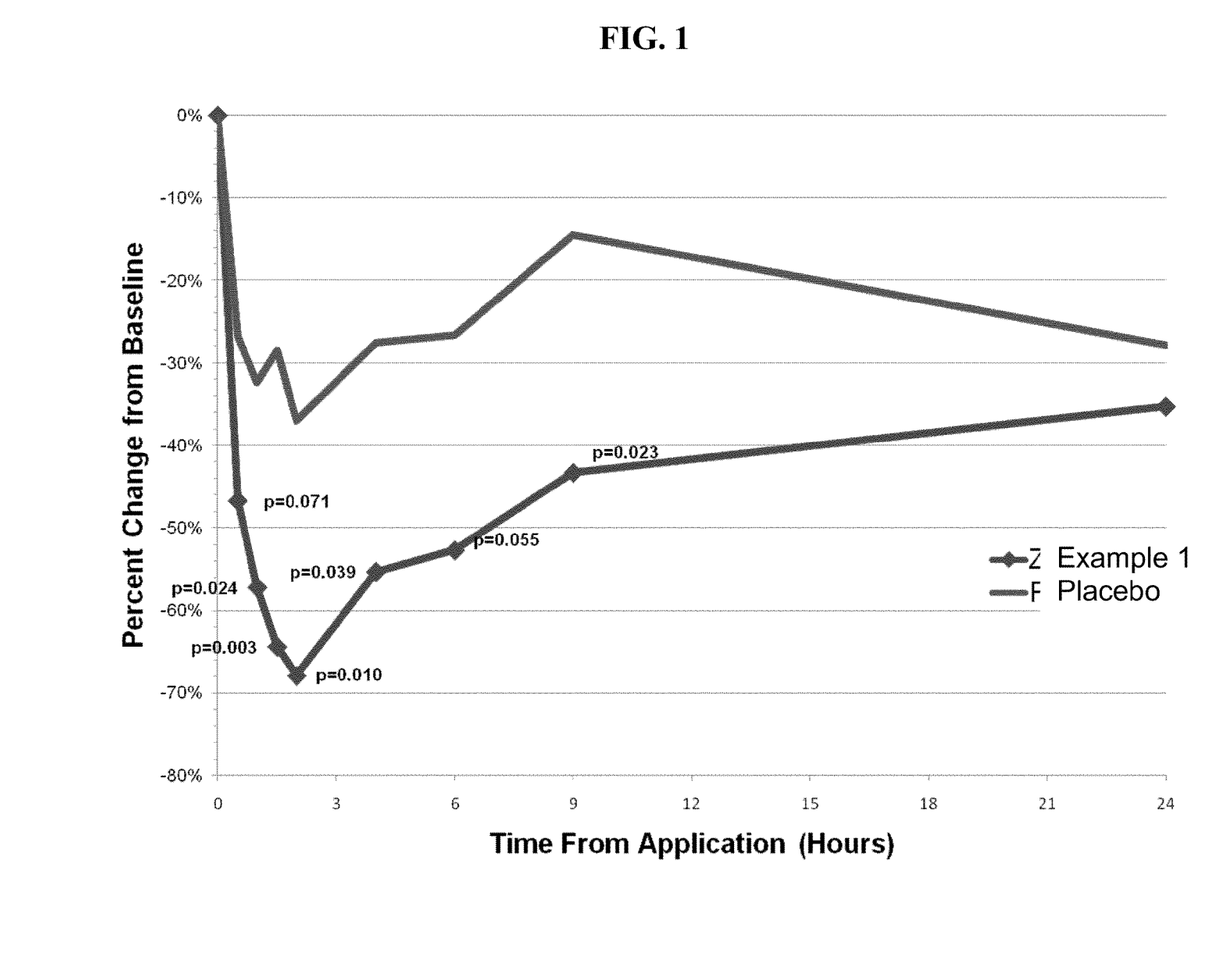
FIG. 1 shows a plot of pain scores using the numeric pain rating scale (NPRS) over a period of 24 hours.
Figure 2:
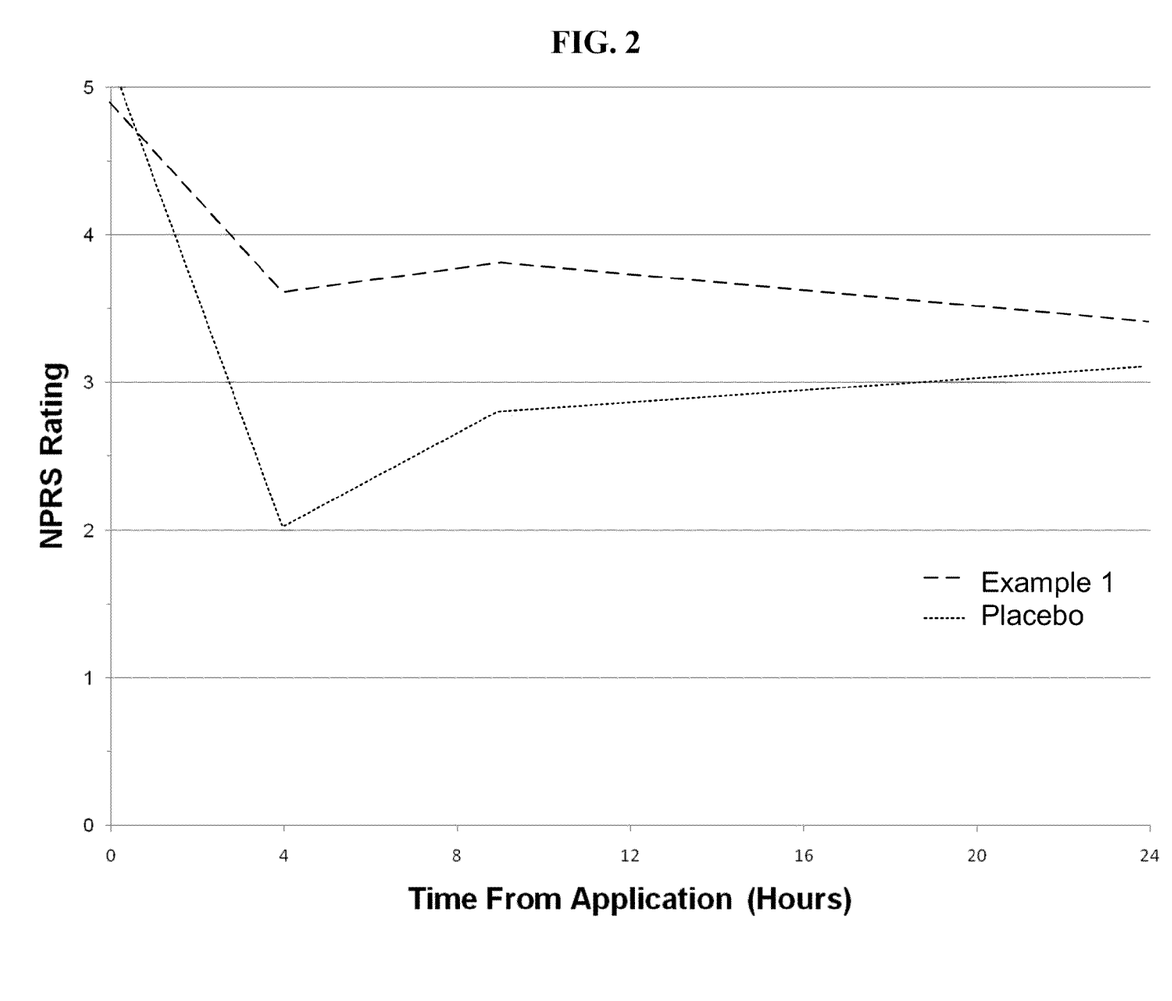
FIG. 2 shows a plot of allodynia intensity using the numeric pain rating scale (NPRS) over a period of 24 hours.

The Formulation of Example 1 was tested on 23 human subjects suffering from post herpetic neuropathy in a double-blind, cross-over study. An approximately 1 millimeter layer of the formulation was applied to a skin area where the human subject was suffering from the pain. The formulation solidified into a soft coherent solid layer and was removed by peeling after 60 min. The pain scores of each of the subjects were recorded with a visual analog pain scale. The mean pain score in the active arm began to show significantly more reduction than the placebo arm as soon as about 30 minutes following the application of the formulation and the reduction was approximately 2-fold greater for the active arm vs. the placebo arm. Pain score reduction of the formulation continued after the removal of the formulation and remained more than 2-fold greater than the placebo for more than 9 hours. The pain scores are shown in FIG. 1. The patients also experienced more allodynia reduction with the active arm than with the placebo arm. Results are shown in FIG. 2. This example indicates that following only one hour application of the formulation, significant pain and allodynia reduction occurred, and the effect can last for more than 9 hours.

Example 4

Treatment of Neuropathic Pain Caused by Post Herpetic Neuropathy

By applying the formulation layer as described in Example 3 at 0.3 mm thick and leaving on the skin for about 2 hours after the application, substantially all of the water present in the formulation will evaporate and the delivery of the local anesthetic substantially stops, though the analgesic effect continues.

Example 5

Viscosity Testing of the Formulations

The following outlines the testing procedures for measuring the viscosity of formulations of the present invention.

1. The samples that need to be tested are removed from the refrigerator and allow them to equilibrate to room temperature for at least 1 hour before handling. The samples need to equilibrate to laboratory temperature before handling.

2. Using a balance, place the empty small sample adapter (13R) on the balance, and press the tare button. Once the adapter has been tared, fill it with sample material to approximately ⅓ of the total weight (about 7 grams). Tap the adapter on a hard surface for several seconds to remove any entrapped air that might be present in the bottom. Continue to fill the sample adapter ⅓ at a time with additional sample material while tapping to remove entrapped air until the sample weight is 20 to 21 grams (maximum).

3. Using a balance centrifuge, spin the sample in the adapter for approximately 30 seconds at a high speed (approximately 4000 rpm) in order to remove any additional air bubbles within the sample.

4. After centrifuging, add additional sample material (about 1 gram) to obtain a final sample weight that is 21 to 22 grams. Record the sample weight (in grams).

5. Set the temperature controller on the viscometer to 23±2° C. Equilibrate the sample in the small sample adapter. Using a thermometer, insert the probe no more than 1 cm into the center of the sample, away from the adapter walls.

6. The sample is now ready to be tested on the viscometer. Insert the sample adapter into the sample adapter holder, align the groove, and lock into place. Remove the back holder supporting the sample adapter by unscrewing the nut located behind the spindle coupling nut module. Align the spindle coupling link with the viscometer coupling nut, and rotate the spindle clockwise. Replace the back holder, submerging the spindle in the middle of the sample holder at the same time. Avoid sample perturbation as much as possible. Screw the nut maintaining the back adapter behind the spindle coupling nut module. The spindle should be immersed in the sample up to the middle of the shaft indentation for the viscosity measurement. Failure to immerse the spindle up to the middle of the shaft indentation could result in a faulty viscosity reading.

7. Once the spindle is firmly in place, press the "SET SPEED" key once, and use the t or j. arrows to set the spindle speed to 4.0 rpm. Press the "SET SPEED" key again. Once the proper speed (4.0 rpm) and spindle (7) are shown in the display, set the timer to countdown from 2 minutes.

8. Simultaneously start the timer and press the "MOTOR ON/OFF" key to begin the viscosity measurement. Allow the reading to equilibrate for 2 minutes before recording the viscosity reading and % torque value.

9. If the reading is out of the viscometer's range (% torque reading >100.0%), the cp and torque reading will display EEEE. At this point, turn off the motor, change the speed to the next lowest setting, and re-start the timer for 2 minutes. Turn the motor and timer on simultaneously, and allow the reading to equilibrate for 2 minutes before recording the torque and viscosity values. If the torque and viscosity are still out-of-range (EEEE) continue to incrementally reduce the speed, and re-run the sample until % T and viscosity values are in range.

10. After an equilibration time of 2 minutes has elapsed, record the % torque and viscosity values. Press the motor key off. At this point, unlock and carefully remove the sample adapter from the sample adapter holder. Remove the spindle from the viscometer by holding the viscometer coupling nut and rotating the spindle counter clockwise.

11. Remove the excess sample material from the spindle. The remaining sample in the sample adapter can be placed in the waste container.

Example 6

The viscosity of the formulation primarily impacts the difficulty of squeezing the product out of the tube and spreading the product on the skin. Lower viscosities are easier for both expulsion out of their containers and application to the skin, however excessively low viscosities can make the product unusable. At overly low viscosities, the formulation may drip excessively out of the tube or run after application to the skin.

Several formulations were produced with varying viscosities and have demonstrated a various viscosity ranges. The following formulations were produced and evaluated for wear properties. Formulation 1 with a viscosity of ~28 k centipoise was easy to apply and spread, but was somewhat runny. Formulations 2 and 3 showed slightly higher viscosities along with decreased tendency to run. Formulations 4 and 5 had yet higher viscosities, but were still easy to squeeze from the tube and very easily spread in a flat layer. These higher viscosity formulations showed lower tendency to run. Formulation 6 with a viscosity of ~828 k was noticeably thicker and required more effort to dispense and spread, but was still suitable for use for some applications, but would be less desirable for very sensitive skin surfaces, such as skin surfaces suffering from allodynia.

| Formulation | 1 | 2 | 3 | 3A | 3B | 4 | 5 | 6 |
| --- | --- | --- | --- | --- | --- | --- | --- | --- |
| Viscosity (centipoises) | 28,460 | 47,800 | 67,800 | 79,500 | 122,500 | 370,500 | 454,500 | 828,500 |
| Ingredients | | | | | | | | |
| Lidocaine (base) | 7.00% | 7.00% | 7.00% | 7.00% | 7.00% | 7.00% | 7.00% | 7.00% |
| Tetracaine (base) | 7.00% | 7.00% | 7.00% | 7.00% | 7.00% | 7.00% | 7.00% | 7.00% |

-continued

| Formulation | 1 | 2 | 3 | 3A | 3B | 4 | 5 | 6 |
|---|---|---|---|---|---|---|---|---|
| Purified Water | 54.27% | 37.94% | 51.87% | 39.94% | 35.94 | 35.94% | 25.94% | 25.94% |
| DiCalcium Phosphate | — | 24.00% | — | 18.00% | 27.00 | 27.00% | 36.00% | 36.00% |
| Polyvinyl Alcohol | 21.60% | 12.00% | 24.00% | 14.00% | 14.00 | 14.00% | 12.00% | 12.00% |
| White Petrolatum | 8.00% | 10.00% | 8.00% | 10.00% | 5.00% | 5.00% | 10.00% | 10.00% |
| Span 40 (Sorbitan Monopalmitate) | 2.00% | 2.00% | 2.00% | — | — | 4.00% | 2.00% | 2.00% |
| Span 60 (Sorbitan Monostearate) | — | — | — | 4.00% | 4.00% | | | |
| Methylparaben | 0.10% | 0.05% | 0.10% | 0.05% | 0.05% | 0.05% | 0.05% | 0.05% |
| Propylparaben | 0.03% | 0.01% | 0.03% | 0.01% | 0.01% | 0.01% | 0.01% | 0.01% |
| Total | 100.00% | 100.00% | 100.00% | 100.00% | 100.00% | 100.00% | 100.00% | 100.00% |

Example 7

The total water content of the formulation is significant primarily from the standpoint of chemical stability and drying time. It has been shown that in aqueous solution, tetracaine hydrolyzes to 4-butylaminobenzoic acid (4-BABA) and 2-dimethylaminoethanol (DMAE). Thus, degradation products in the formulation should be minimized in order to ensure optimal potency and purity of the formulation. Studies of various formulations (see table below) have shown that the levels of 4-BABA in the formulation correlate to the total water content in the formulation. In the sense that it is desirable to maintain levels of 4-BABA below 3% after 24 months of storage at 5° C. (shelf-life), for example, it would be desirable to ensure total water content remains below ~50%.

| Formulation | 7 | 8 | 9 | 10 | 11 |
|---|---|---|---|---|---|
| Water Content | 29.54% | 31.94% | 42.82% | 48.88% | 51.87% |
| 4-BABA level after 12 months storage at 5° C. | 0.75% | 0.82% | 1.09% | 1.42% | 1.50% |
| Projected 4-BABA level after 24 months storage at 5° C. | 1.50% | 1.64% | 2.18% | 2.84% | 3.00% |
| Ingredients | | | | | |
| Lidocaine (base) | 7.00% | 7.00% | 7.00% | 7.00% | 7.00% |
| Tetracaine (base) | 7.00% | 7.00% | 7.00% | 7.00% | 7.00% |
| Purified Water | 29.54% | 31.94% | 42.82% | 48.88% | 51.87% |
| DiCalcium Phosphate | 32.40% | 30.00% | — | — | — |
| Polyvinyl Alcohol | 12.00% | 12.00% | 19.77% | 27.00% | 24.00% |
| White Petrolatum | 10.00% | 10.00% | — | 8.00% | 8.00% |
| Span 40 (sorbitan Monopalmitate) | 2.00% | 2.00% | 3.30% | 2.00% | 2.00% |
| Methylparaben | 0.05% | 0.05% | 0.09% | 0.10% | 0.10% |
| Propylparaben | 0.01% | 0.01% | 0.02% | 0.02% | 0.03% |
| Corn Starch | — | — | 20.00% | — | — |
| Total | 100.00% | 100.00% | 100.00% | 100.00% | 100.00% |

It is also notable that the total water content has a direct impact on the drying time of the formulation. Since the evaporation of water causes the formulation to form a solidified layer, it is expected that total water content will directly impact drying time. Several formulations were studied to assess the impact of water content on drying time, and the results provided below indicate that a formulation with ~30% water was completely dry to the touch in approximately 10 minutes, whereas formulations with 40% and 54% water required approximately 30 and 60 minutes, respectively, to be dry to the touch. Dry to the touch means the surface of the formulation layer is solidified enough so that a light touch by a finger does not remove any formulation from the layer.

| Formulation | 12 | 13 | 14 |
|---|---|---|---|
| Water Content | 31.94% | 39.94% | 54.27% |
| Drying Time | Less than 10 minutes | Between 10-30 minutes | Between 30-60 minutes |
| Ingredients | | | |
| Lidocaine (base) | 7.00% | 7.00% | 7.00% |
| Tetracaine (base) | 7.00% | 7.00% | 7.00% |
| Purified Water | 31.94% | 39.94% | 54.27% |
| DiCalcium Phosphate | 30.00% | 18.00% | — |
| Polyvinyl Alcohol | 12.00% | 14.00% | 21.60% |
| White Petrolatum | 10.00% | 10.00% | 8.00% |
| Span 40 (sorbitan Monopalmitate) | 2.00% | — | 2.00% |
| Span 60 (sorbitan Monostearate) | — | 4.00% | — |
| Methylparaben | 0.05% | 0.05% | 0.10% |
| Propylparaben | 0.01% | 0.01% | 0.03% |
| Total | 100.00% | 100.00% | 100.00% |

Example 8

Since the formulations herein may be stored in refrigerated conditions, the impact of very cold, freezing, or cycling temperatures (freeze-thaw) on the formulations can be considered for improving the formulation. Freeze-thaw cycles may cause the PVA molecules in the formulations to crosslink, resulting in a dramatic increase in viscosity which may make the formulation difficult to spread on skin. A series of cycling (freeze-thaw) studies was performed on several formulations in order to assess the impact of exposure to multiple "freeze-thaw" cycles. One freeze-thaw cycle is defined as exposure to freezing conditions (i.e. −20° C.) for 2-3 days followed by exposure to thawing conditions (i.e. 25° C.) for 2-3 days. A more robust formulation will show less increase in viscosity after exposure to multiple freeze-thaw cycles.

Several formulations have been developed and subjected to freeze-thaw cycles. Viscosity at baseline and after each freeze-thaw cycle was measured using the method outlined in Example 5.

The data gathered on the formulations below indicate that the water to PVA ratio has an impact on the resistance to freeze/thaw exposures. Formulations having a water:PVA ratio greater than 2.5 demonstrated less pronounced viscosity increases after exposure to multiple freeze/thaw cycles, as shown in the table below.

| | Formulation | | | | |
|---|---|---|---|---|---|
| | 15 | 16 | 17 | 18 | 19 |
| Water/PVA ratio | 2.16 | 2.46 | 2.57 | 2.85 | 3.16 |
| Ingredients | | | | | |
| Lidocaine (base) | 7.00% | 7.00% | 7.00% | 7.00% | 7.00% |
| Tetracaine (base) | 7.00% | 7.00% | 7.00% | 7.00% | 7.00% |
| Purified Water | 25.94% | 29.54% | 35.94% | 39.94% | 37.94% |
| DiCalcium Phosphate | 36.00% | 32.40% | 27.00% | 18.00% | 24.00% |
| Polyvinyl Alcohol | 12.00% | 12.00% | 14.00% | 14.00% | 12.00% |
| White Petrolatum | 10.00% | 10.00% | 5.00% | 10.00% | 10.00% |
| Span 40 (Sorbitan Monopalmitate) | 2.00% | 2.00% | — | — | 2.00% |
| Span 60 Sorbitan Monostearate) | — | — | 4.00% | 4.00% | — |
| Methylparaben | 0.05% | 0.05% | 0.05% | 0.05% | 0.05% |
| Propylparaben | 0.01% | 0.01% | 0.01% | 0.01% | 0.01% |
| Total | 100.00% | 100.00% | 100.00% | 100.00% | 100.00% |
| Initial Viscosity | 454,500 | 146,000 | 122,500 | 79,500 | 47,800 |
| Freeze/Thaw Viscosity Results | | | | | |
| 1 cycle | 7,200,000 | 436,500 | 170,000 | 94,500 | 29,440 |
| 2 cycles | >8,000,000 | 427,000 | 226,500 | 114,000 | 29,160 |
| 3 cycles | >8,000,000 | 1,150,000 | 210,000 | 146,000 | 33,080 |
| 4 cycles | >8,000,000 | 2,385,000 | 227,500 | 87,000 | 46,400 |
| 5 cycles | >8,000,000 | 3,310,000 | 333,000 | 137,500 | 38,000 |

-continued

| | Formulation | | | | |
|---|---|---|---|---|---|
| | 15 | 16 | 17 | 18 | 19 |
| Freeze/Thaw Viscosity Increase Multiple | | | | | |
| 1 cycle | 16 | 3 | 1 | 1 | 1 |
| 2 cycles | >18 | 3 | 2 | 1 | 1 |
| 3 cycles | >18 | 8 | 2 | 2 | 1 |
| 4 cycles | >18 | 16 | 2 | 1 | 1 |
| 5 cycles | >18 | 23 | 3 | 2 | 1 |

Example 9

Two solid-forming local anesthetic formulations were made and their compositions are listed in the following table. The formulations are identical except Formulation 20 used Span 40 (Sobitan Monopalmitate) as emulsifying agent and Formulation 21 used Span 60 (Sorbitan Monostearate). After about three months, Formulation 20 showed significantly more phase separation that Formulation 21.

| | Formulation | |
|---|---|---|
| Ingredients | 20 | 21 |
| Lidocaine | 7.00% | 7.00% |
| Tetracaine | 7.00% | 7.00% |
| Purified Water | 35.94% | 35.94% |
| DiCalcium Phosphate | 27.00% | 27.00% |
| Polyvinyl Alcohol | 14.00% | 14.00% |
| White Petrolatum | 5.00% | 5.00% |
| Span 40 (Sobitan Monopalmitate) | 4.00% | — |
| Span 60 (Sorbitan Monostearate) | — | 4.00% |
| Methylparaben | 0.05% | 0.05% |
| Propylparaben | 0.01% | 0.01% |
| Total | 100.00% | 100.00% |
| Initial Viscosity | 132,000 | 122,500 |
| Water/PVA ratio | 2.57 | 2.57 |

While the invention has been described with reference to certain preferred embodiments, those skilled in the art will appreciate that various modifications, changes, omissions, and substitutions can be made without departing from the spirit of the invention. It is therefore intended that the invention be limited only by the scope of the appended claims.

What is claimed is:

1. A method of treating neuropathic pain in a subject, comprising:
    applying a layer of a solid-forming local anesthetic formulation to a skin surface of a human experiencing neuropathic pain, said solid-forming local anesthetic formulation comprising a local anesthetic agent, water, and at least one polymer selected from the group consisting of polyvinyl alcohol, polyvinylpyrrolidone, ethylcellulose, or combinations thereof, and being in the state of a semi-solid before being applied to said skin surface; and
    maintaining said layer of said formulation on said skin surface for a period of time sufficient to allow said layer of said formulation to transdermally deliver the local anesthetic to the subject and to form a layer of a coherent soft solid after a sufficient amount of water is evaporated from said layer of said formulation,
    wherein the solid-forming local anesthetic formulation is formulated to deliver the local anesthetic agent to the subject until substantially all of the water present in the formulation has evaporated and delivery of the local anesthetic stops or slows significantly so as to have no therapeutic effect thereafter, and wherein the solid-forming local anesthetic formulation provides relief from said neuropathic pain within about 45 minutes after application to the skin surface.

2. The method of claim 1, wherein the solid-forming local anesthetic formulation is maintained on the skin surface of the subject for a period of time of about 30 minutes to 2 hours.

3. The method of claim 1, wherein the skin surface is directly over the neuropathic pain.

4. The method of claim 1, wherein the method further comprises the step of removing the solid-forming local anesthetic formulation after it forms said layer of coherent soft solid by peeling a coherent soft solid from the skin at from 20 to 120 minutes after application.

5. The method of claim 1, wherein the solid-forming local anesthetic formulation is applied to said skin surface as a layer with a thickness from 0.1 to 3.0 millimeters.

6. The method of claim 1, wherein the solid-forming local anesthetic formulation is applied to said skin surface as a layer with a thickness from 0.2 to 1.5 millimeters.

7. The method of claim 1, wherein said local anesthetic agent includes tetracaine.

8. The method of claim 7, wherein the tetracaine comprises 6 wt % to 8 wt % of the solid-forming local anesthetic formulation before said formulation is applied to said skin surface.

9. The method of claim 1, wherein said local anesthetic agent includes lidocaine.

10. The method of claim 9, wherein the lidocaine comprises 6 wt % to 8 wt % of the solid-forming local anesthetic formulation before said formulation is applied to said skin surface.

11. The method of claim 1, wherein said local anesthetic agent is a eutectic mixture of lidocaine and tetracaine.

12. The method of claim 1, wherein the local anesthetic agent is selected from the group consisting of lidocaine, tetracaine, prilocaine, ropivacaine, bupivacaine, and mixtures thereof.

13. The method of claim 1, wherein the local anesthetic is in base form.

14. The method of claim 1, wherein the solid-forming local anesthetic formulation is formulated to provide relief from said neuropathic pain within about 30 minutes after application to the skin surface.

15. The method of claim 1, wherein the solid-forming local anesthetic formulation is formulated to provide pain relief for at least 9 hours after an application time of at least 45 minutes.

16. The method of claim 1, wherein the solid-forming local anesthetic formulation includes at least about 15 wt % water before being applied to said skin surface.

17. The method of claim 1, wherein the solid-forming local anesthetic formulation includes at least about 22 wt % water before being applied to said skin surface.

18. The method of claim 1, wherein the solid-forming local anesthetic formulation includes at least about 50 wt % water before being applied to said skin surface.

19. The method of claim 1, wherein the polymer includes polyvinyl alcohol.

\* \* \* \* \*